(12) United States Patent
Bange et al.

(10) Patent No.: US 7,359,753 B2
(45) Date of Patent: Apr. 15, 2008

(54) SYSTEM AND METHOD FOR RF WAKE-UP OF IMPLANTABLE MEDICAL DEVICE

(75) Inventors: Joseph E. Bange, Eagan, MN (US); Allan T. Koshiol, Lino Lakes, MN (US); Karen M. Lent, Stillwater, MN (US); Paul Holmquist, Andover, MN (US); Thomas J. Harris, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 280 days.

(21) Appl. No.: 11/101,142

(22) Filed: Apr. 7, 2005

(65) Prior Publication Data

US 2005/0288738 A1     Dec. 29, 2005

Related U.S. Application Data

(60) Provisional application No. 60/560,171, filed on Apr. 7, 2004.

(51) Int. Cl.
*A61N 1/00* (2006.01)
(52) U.S. Cl. .......................... 607/32; 607/60
(58) Field of Classification Search ............ 607/32, 607/60, 2; 128/903; 455/73
See application file for complete search history.

(56) References Cited

U.S. PATENT DOCUMENTS

| | | | |
|---|---|---|---|
| 3,914,586 A | 10/1975 | McIntosh | |
| 4,562,841 A | 1/1986 | Brockway et al. | |
| 5,171,977 A | 12/1992 | Morrison | |
| 5,300,093 A | 4/1994 | Koestner et al. | |
| 5,342,408 A | 8/1994 | deCoriolis et al. | |
| 5,486,200 A | 1/1996 | Lindemans | |
| 5,630,835 A | 5/1997 | Brownlee | |
| 5,881,101 A | 3/1999 | Furman et al. | |
| 6,167,310 A | 12/2000 | Grevious | |
| 6,263,246 B1 | 7/2001 | Goedeke et al. | |

(Continued)

FOREIGN PATENT DOCUMENTS

WO     WO-9500202 A1     1/1995

(Continued)

OTHER PUBLICATIONS

"International Search Report and Written Opinion of the International Searching Authority, for Application No. PCT/US2005/011639, date mailed Aug. 26, 2005", 12 Pages.

(Continued)

*Primary Examiner*—Carl Layno
*Assistant Examiner*—Jon-Eric Morales
(74) *Attorney, Agent, or Firm*—Schwegman, Lundberg & Woessner, P.A.

(57) ABSTRACT

A telemetry system is presented for enabling radio-frequency (RF) communications between an implantable medical device and an external device in a manner which reduces the power requirements of the implantable device by duty cycling its RF circuitry. A wakeup scheme for the implantable device is provided in which the external device transmits a data segment containing a repeating sequence of special wakeup characters in order to establish a communications session with the implantable device. The wakeup scheme may be designed to operate in the context of a handshaking protocol for collision avoidance.

18 Claims, 2 Drawing Sheets

U.S. PATENT DOCUMENTS

| | | | |
|---|---|---|---|
| 6,336,903 B1* | 1/2002 | Bardy | 600/508 |
| 6,562,001 B2 | 5/2003 | Lebel et al. | |
| 6,648,821 B2* | 11/2003 | Lebel et al. | 600/300 |
| 7,110,823 B2 | 9/2006 | Whitehurst et al. | |
| 2002/0019606 A1* | 2/2002 | Lebel et al. | 604/66 |
| 2002/0049480 A1* | 4/2002 | Lebel et al. | 607/60 |
| 2002/0065540 A1* | 5/2002 | Lebel et al. | 607/60 |
| 2003/0114897 A1* | 6/2003 | Von Arx et al. | 607/60 |
| 2003/0114898 A1* | 6/2003 | Von Arx et al. | 607/60 |
| 2005/0240245 A1 | 10/2005 | Bange et al. | |
| 2005/0283208 A1 | 12/2005 | Von Arx et al. | |
| 2006/0116744 A1 | 6/2006 | Von Arx et al. | |

FOREIGN PATENT DOCUMENTS

| | | |
|---|---|---|
| WO | WO-03053515 A1 | 7/2003 |
| WO | WO-2005099817 A1 | 10/2005 |

OTHER PUBLICATIONS

"U.S. Appl. No. 10/025,223 Final Office Action mailed Aug. 16, 2004", 8 Pages.

"U.S. Appl. No. 10/025,223 Final Office Action mailed Sep. 10, 2004", 7 Pages.

"U.S. Appl. No. 10/025,223 Non-Final Office Action mailed Mar. 1, 2005", 6 Pages.

"U.S. Appl. No. 10/025,223 Non-Final Office Action mailed Mar. 19, 2004", 5 Pages.

"U.S. Appl. No. 10/025,223 Notice of Allowance mailed Aug. 10, 2005", 4 Pages.

"U.S. Appl. No. 10/870,324 Non-Final Office Action mailed Jun. 27, 2007", 6 Pages.

"U.S. Appl. No. 11/101,196 Non Final Office Action mailed Mar. 29, 2007", 6 Pages.

"U.S. Appl. No. 11/101,196 Notice of Allowance mailed Aug. 27, 2007", 4 Pages.

"U.S. Appl. No. 11/101,196 Response filed Jun. 29, 2007 to Non Final Office Action mailed Mar. 29, 2007", 8 Pages.

* cited by examiner

SYSTEM AND METHOD FOR RF WAKE-UP OF IMPLANTABLE MEDICAL DEVICE

CROSS-REFERENCE TO RELATED APPLICATION(S)

This application claims the benefit of U.S. Provisional Application No. 60/560,171, filed on Apr. 7, 2004, under 35 U.S.C. § 119(e), which is hereby incorporated by reference.

FIELD OF THE INVENTION

This invention pertains to implantable medical devices such as cardiac pacemakers and implantable cardioverter/defibrillators. In particular, the invention relates to a system and method for implementing telemetry in such devices.

BACKGROUND

Implantable medical devices, including cardiac rhythm management devices such as pacemakers and implantable cardioverter/defibrillators, typically have the capability to communicate data with a device called an external programmer via a radio-frequency telemetry link. One use of such an external programmer is to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

Telemetry systems for implantable medical devices utilize radio-frequency (RF) energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand that can be positioned in proximity to the implanted device. The implantable device also generates and receives radio signals by means of an antenna, typically formed by a wire coil wrapped around the periphery of the inside of the device casing. Most conventional radio-frequency telemetry systems used for implantable medical devices such as cardiac pacemakers utilize inductive coupling between the antennas of the implantable device and an external programmer in order to transmit and receive RF signals. Because the induction field produced by a transmitting antenna falls off rapidly with distance, such systems require close proximity between the implantable device and a wand antenna of the external programmer in order to work properly, usually on the order of a few inches. This requirement is an inconvenience for a clinician and limits the situations in which telemetry can take place.

Wireless radio-frequency communication over greater distances requires the use of far-field telemetry. Communication using far-field radiation can take place over much greater distances, which makes it more convenient to use an external programmer. Also, the increased communication range makes possible other applications of the telemetry system such as remote monitoring of patients and communication with other types of external devices such as network access points. In order for a substantial portion of the energy delivered to an antenna to be emitted as far-field radiation, the wavelength of the driving signal should not be very much larger than the length of the antenna. Far-field radio-frequency communications with an antenna of a size suitable for use in an implantable device therefore requires a carrier in the frequency range of between a few hundred MHz to a few GHz. Active transmitters and receivers for this frequency range require special RF components (typically including SiGe or GaAs semiconductor devices) that consume a significant amount of power (typically tens of milliwatts). Implantable medical devices, however, are powered by a battery contained within the housing of the device that can only supply a limited amount of continuous power before it fails. When the battery fails in an implantable device, it must be replaced which necessitates a re-implantation procedure. Power conservation is thus an important design objective in wireless telemetry systems for implantable medical devices.

SUMMARY

The present invention relates to a telemetry system for enabling radio-frequency (RF) communications between an implantable medical device and an external device in a manner which reduces the power requirements of the implantable device. In accordance with the invention, the external device is programmed to transmit a data segment containing a repeating sequence of special wakeup characters in order to establish a communications session with the implantable device. The implantable device is programmed to power up its transmitter and receiver for a specified time window at periodic intervals defined by the wakeup timer and wait for receipt of one of the special wakeup characters transmitted by the external device. The implantable device maintains its transmitter and receiver in a powered-up state upon receipt of a special character and for as long as consecutive special wakeup characters continue to be received, to transmit an acknowledge signal to the external device upon receipt of at least one character other than a special wakeup character, and then to wait a specified period of time for a response from the external device. The external device and the implantable device then attempt to establish a communications session when a response to the acknowledge signal is received by the implantable device.

DETAILED DESCRIPTION

Figure 1:
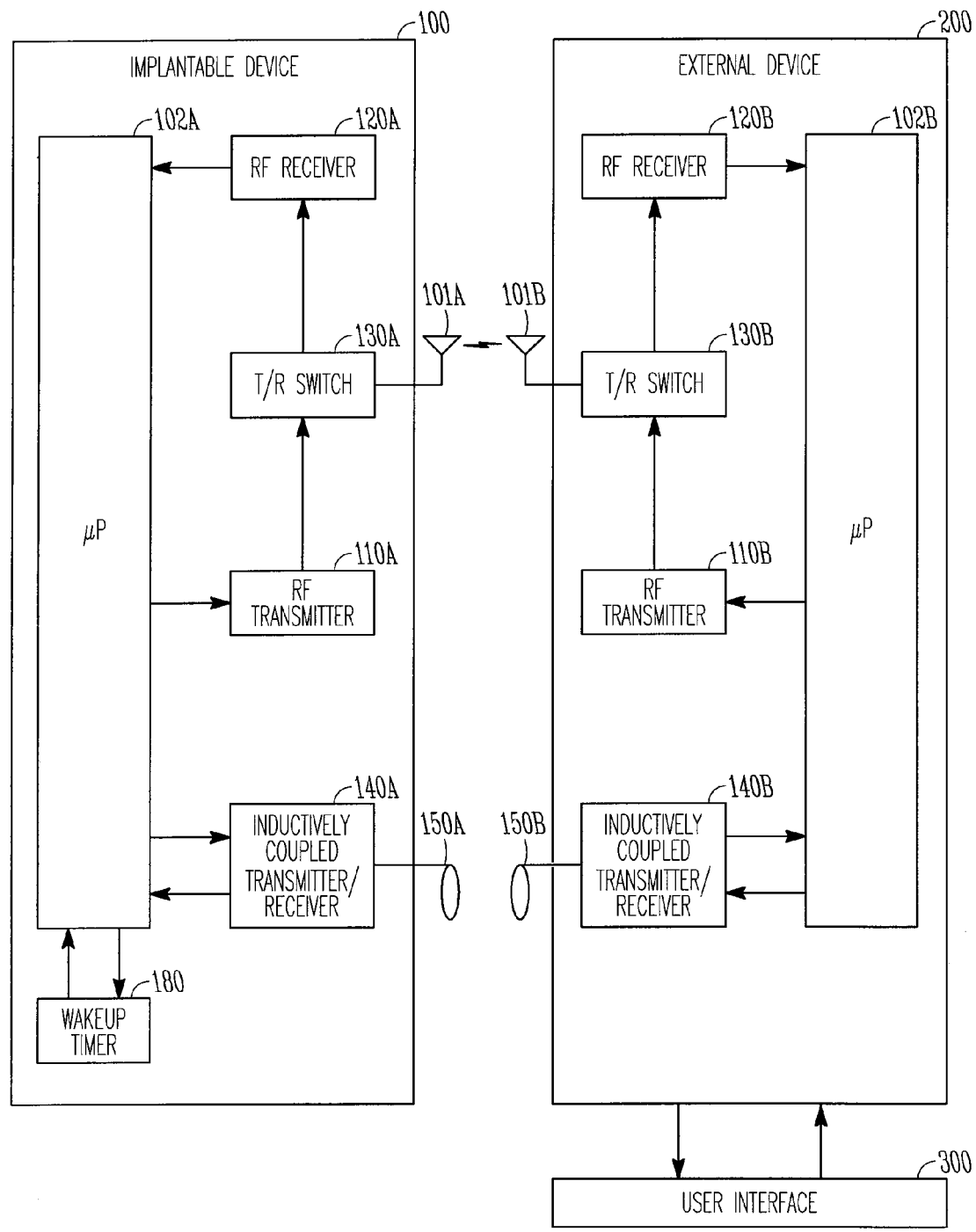
FIG. 1 is a block diagram of a telemetry system for an implantable device and an external device.

The present invention is a system and method for providing far-field RF telemetry between an implantable medical device and an external device in which power consumption by the implantable device is lessened by managing the duty cycle of the RF transmitting and receiving components. Long-range RF telemetry circuitry (i.e., the transmitter and receiver) typically requires power on the order of tens of milliwatts in order to operate. Implantable cardiac devices in use today, on the other hand, are usually designed to operate with average power in the microwatt range. This means that the RF telemetry circuitry must be duty cycled down in order to meet the power budget of such devices. Previous examples of duty cycling for implantable devices are described in U.S. Pat. No. 5,342,408 and U.S. patent application Ser. No. 10/025,223, entitled "A TELEMETRY DUTY CYCLE MANAGEMENT SYSTEM FOR AN IMPLANTABLE MEDIACL DEVICE", presently assigned to Cardiac Pacemakers, Inc., and hereby incorporated by reference.

The RF telemetry circuitry of an implantable device can either be powered up or down, referred to as awake and sleep states, respectively. Duty cycling of the implantable device's RF telemetry circuitry can be implemented by a wakeup timer which defines periodic wakeup intervals at which the implantable device powers up its RF circuitry and listens for a transmission from an external device for a specified period of time, referred to as a wakeup window. Upon acknowledging the transmission from the external device, a communications session can be established by a handshaking protocol, and data can then be transferred between the devices. In order to minimize power consumption, it is desirable for the RF circuitry of the implantable device to be powered up for as short a time as possible at each wakeup interval while still being able to reliably recognize session requests from the external device. If the implantable device recognizes a session request from the external device during its wakeup window, it remains awake long enough to establish a communications session with the external device; otherwise, the implantable device returns to a sleep state until the next wakeup interval occurs.

In accordance with the present invention, the external device is programmed to transmit a data frame containing a repeating sequence of special wakeup characters when it is desired to establish a communications session with the implantable device. The implantable device is programmed to power up its transmitter and receiver for a specified wakeup window at periodic intervals defined by its wakeup timer and wait for receipt of one of the special wakeup characters transmitted by the external device. The implantable device maintains its transmitter and receiver in a powered-up state upon receipt of a special character and for as long as consecutive special wakeup characters continue to be received, and transmits an acknowledge signal to the external device upon receipt of at least one character other than a special wakeup character. After transmitting the acknowledge signal, the implantable device then waits a specified period of time for a response from the external device. When a response to the acknowledge signal is received by the implantable device, the external device and the implantable device are programmed to establish a communications session by a handshaking protocol. During a communications session, the RF transmitter and receiver of the implantable device may then either be maintained in the powered-up state for the duration of the communications session or powered down at prescribed intervals according to a defined protocol.

As described in detail below, the wakeup scheme may be designed to work in the context of a medium access control (MAC) protocol by which network participants contend for access to the wireless medium. Also, in one embodiment, the implantable device and the external device communicate by a transmission code which provides a DC balanced data stream such as 8b/10b. Such bit balanced data streams are advantageous in RF communications. In order for the special wakeup character to be invariant, the special wakeup character may be selected as a bit balanced sequence which is not changed by the transmission code.

In another particular embodiment, the external device is a remote monitor (RM) which operates to periodically collect data from the implantable device. The remote monitor may thus include a wakeup timer and be programmed to transmit a plurality of special wakeup characters to the implantable device in an attempt to establish a communications session at periodic intervals as defined by its wakeup timer. After the implantable device is awoken by the special wakeup characters, a communications session is established in which the implantable device transmits whatever data it has to the RM. If the implantable device has no data to transmit, however, the communications session is terminated almost immediately after being established. Such empty communications sessions still impose an energy cost upon the implantable device, however, due to the time it takes for the implantable device to wake up, establish a communications session with the RM, indicate that there is nothing to download, and then terminate the session. The total duty cycle of the RF circuitry in the implantable device is thus a function of both its own wakeup interval and the intervals at which the RM attempts to wake up the implantable device. In order to lessen power consumption by the implantable device, therefore, it is desirable for the intervals at which the RM attempts to wake up the implantable device to be such that the number of empty communications sessions is minimized. The remote monitor may thus be further programmed to adjust the periodic intervals at which it transmits a plurality of special wakeup characters to the implantable device in accordance with when previous successful communications sessions have been established such that data was collected. In one particular embodiment, the remote monitor is programmed to establish a communications session and collect data from the implantable device on a daily basis and further programmed to adjust the periodic intervals at which it attempts to wake up the implantable device in accordance with the time of day at which past successful communications sessions were established. In order to be able to respond to an episode, the remote monitor may also be programmed to transmit a plurality of special wakeup characters to the implantable device for establishing a communications session when a user command is received via a user interface.

1. Exemplary Hardware Components

FIG. 1 shows the primary telemetry components of an external device 200 and an implantable medical device 100. In this functional block diagram, the components are shown as being identical in each device. In this exemplary embodiment, the external device and the implantable device are microprocessor-based devices each having a controller 102a or 102b that includes a microprocessor and memory for data and program storage that supervises overall device operation as well as telemetry. Code executed by the controller also implements the duty cycle management schemes to be described below. The implantable device 100 may be a cardiac rhythm management device such as a pacemaker or implantable cardioverter/defibrillator, while the external device 200 may be an external programmer or a data-gathering device such as remote monitor. A user interface 300 (e.g., a keyboard and monitor) enables a user such as a clinician to direct the operation of the external device.

A long-range RF receiver 120a or 120b and a long-range RF transmitter 110a or 110b are interfaced to the microprocessor 102a or 102b in the implantable device and the external device, respectively. Also in each device, the transmitter and receiver are coupled to an antenna 101a or 101b through a transmit/receive switch 130a or 130b. The transmit/receive switches 130a and 130b are controlled by the microprocessor and either passes radio-frequency signals from the transmitter to the antenna or from the antenna to the receiver. To effect communications between the devices, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The implantable device also incorporates a means by which the controller can power up or power down the RF receiver and/or transmitter in order to manage duty cycles in the manner described below. A wakeup timer 180 for defining the RF duty cycle is also shown for the implantable device, and this timer can either be implemented in code executed by the controller or can be discrete components. FIG. 1 also shows an inductively coupled transmitter/receiver 140a or 140b and antenna 150a or 150b for the implantable and external devices by which communication may take place without concern for power consumption when the two devices are in close physical proximity to one another.

2. Description of Specific Embodiments

Figure 2:
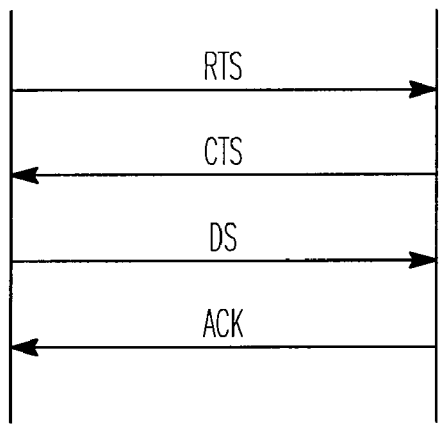
FIG. 2 illustrates a handshaking protocol for collision avoidance.

A wireless telemetry system for implantable medical devices is generally a multiple access network in which a number of network participants share the available bandwidth of the wireless medium. A medium access control (MAC) protocol may be defined which allows each network participant to acquire exclusive access to the medium before transmitting data to an intended recipient. A collision is said to occur when two or more participants attempt to transmit at the same time. In certain networks, collisions may be detected by the sender listening to the medium when a transmission is initiated to determine if other network activity is present. If a collision is detected, the sender ceases transmitting and waits for a random or defined period before trying again. Most wireless transceivers operate in a half-duplex mode, however, and cannot simultaneously transmit and listen for ongoing network activity. MAC protocols for wireless networks therefore typically use out-of-band signaling or a handshaking protocol to minimize the probability of a collision occurring. In an example of the latter type of protocol, a four-way RTS-CTS-DS-ACK exchange as illustrated by FIG. 2 is used to avoid collisions. A network participant who desires to send a message to a particular recipient first transmits a request-to-send (RTS) frame and waits a defined period of time for a clear-to-send (CTS) frame from the intended recipient. All network participants who hear either of the RTS or CTS frames defer their transmissions. Upon receiving the CTS response, the sender can assume that the medium has been exclusively acquired and can then begin transmission of a data segment (DS) to the recipient. If the data is received without errors, the recipient responds with an acknowledge (ACK) frame which frees the medium for access by another participant. The present invention, in various embodiments, may work in the context of any of the medium access control protocols discussed above.

a. Exemplary Wakeup Scheme

Figure 3:
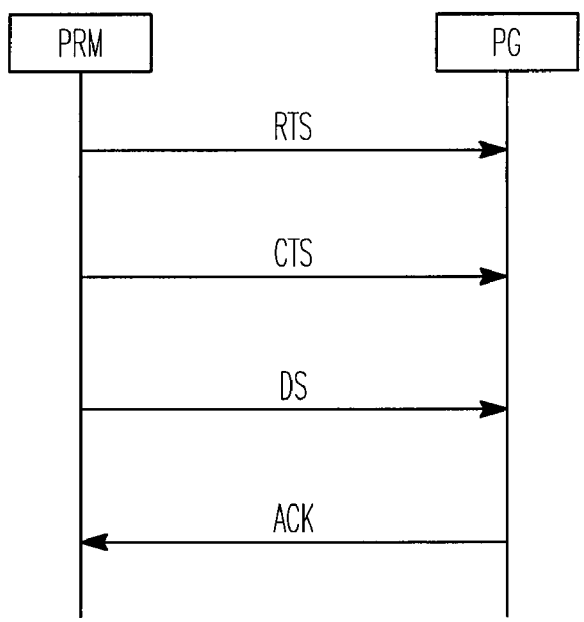
FIG. 3 illustrates a wakeup scheme in accordance with the invention.

A particular embodiment of the invention will now be described with reference to an external programmer or remote monitor (PRM/RM) and an implantable device (referred to as a pulse generator or PG). In this embodiment, the wakeup process works within the framework of a handshaking collision avoidance scheme as described above. In such a scheme, a network participant may transmit a so-called universal broadcast to all other participants in the network by transmitting an RTS-CTS-DS-ACK sequence. The PRM/RM transmits the RTS and CTS frames to cause other participants to defer their transmissions, transmits a data segment DS, and then transmits an ACK frame to release the medium. The wakeup process is illustrated by FIG. 3 and is similar to a universal broadcast with the exception that the PG provides the ACK frame instead of the PRM/RM. The PRM/RM sends out the messages RTS, CTS, and DS using the universal access code. The length of the DS message is set to a large number (e.g., 256 bytes), and the entire data portion of the message area is set to a repeating sequence of a special 10-bit character reserved solely for use as a wakeup indicator. (As described below, the wakeup indicator may be a special 8b10b character.) The PG wakes up periodically (e.g., every 20-30 seconds) and listens for a very short interval to receive the wakeup special character. This short wakeup interval needs to be on the order of slightly longer than twenty bits after the PG's RF receiver has stabilized so that at least one entire 10-bit special character can be received. It is important to note that any normal preamble that is designed to get the PG receiver to its steady state of operation will not be present during the wakeup. An additional time is therefore required, on the order of an additional 10 bits above the standard 20 bits for a total of 30 bits. This means that the minimum wakeup time in this embodiment is 50+bits (10+20+20), which is 440 microseconds at a modulation rate of 113.7 Kbps. The projections below are based on a margin above this of 500 us allowing for a 6-bit margin. If one wakeup special character is received, then the PG will stay awake long enough to receive several more wakeup special characters. If several wakeup special characters are received, the PG stays awake until it no longer receives special characters. After two consecutive non-special characters (e.g., these could be the CRC values of the DS frame), the PG responds with an ACK frame and will now stay awake for an extended period of time. The PRM having successfully received this ACK message will then proceed to perform a discovery process which will contend for message traffic within the protocol framework in order to establish a communications session with the PG.

In the wakeup scheme just described, a problem may arise if two PG's are in range of the PRM/RM when the wakeup sequence is transmitted. If both PG's wake up and respond to the wakeup sequence with an ACK frame, a collision will occur. In a further modification of the scheme, the PRM/RM may therefore be programmed to monitor the RF signal strength after transmission of the wakeup sequence during the expected ACK response time and proceed with the discovery process if there is found to be some RF activity.

An advantage of the wakeup scheme described above is that the PRM/RM is able to quickly establish a communications session with the PG on demand. The PG will be woken up within 20 seconds if the PG wakes up every 20 seconds and wakes up when a special character is being transmitted. (The probability that the PG will be awoken within that time increases with the length of the sequence of repeating special characters transmitted by the PRM/RM.) At the same time, the PG is subjected to a very low duty cycle which lessens the power requirements of operating a far-field RF telemetry system to acceptable levels. For example, an exemplary implantable cardiac rhythm management device may operate at an average current draw on the order of 22 microamps and is designed to last 6 years before a battery replacement is needed. This means that each 305 nanoamps of current draw costs the device one month in longevity. When the RF circuitry is powered up, its current draw is on the order of 4 milliamps. If the device wakes up every 20 seconds and remains powered up for 500 microseconds, the duty cycle is 1/40,000. The average current due to wake ups (but not, of course, including the current necessary for actually performing telemetry) is then (4 mA) (1/40,000)=100 nanoamps, resulting in a longevity cost to the device of just over a week.

b. Choice of Special Wakeup Character

In an embodiment where a DC balanced coding scheme such as 8b/10b is employed, it is desired to know a priori that the wakeup special character is always going to have one value independent of the running disparity (RD) of the 8b/10b encoding. The first step in achieving this goal is to choose a wakeup preamble from the set of valid special characters that is bit balanced. There are 7 such codes that have exactly 5 ones and 5 zeros. Codes that are bit balanced do not change the running disparity after transmission so that successive transmission would be identical values avoiding the inversion that occurs on non-bit balanced codes. The second step is to determine what the initial running disparity is when the data portion of the DS message is sent. Since this message is predetermined, it is a simple matter to determine the running disparity. The RD has an initial negative value (RD−) and starts with the first byte of the access code. The RD is then computed after each of the 8b/10b conversions. The RD at the start of the data portion is then the RD after the two universal access code bytes, the command byte, and the length byte. The proposal for wakeup special character and universal access codes is to choose two of the 7 bit-balanced valid special characters. The values are chosen as:

| Code | Special code name | RD− | RD+ |
| --- | --- | --- | --- |
| Universal Access Code 1: | K28.0 | 0011110100 | 1100001011 |
| Universal Access Code 2: | K28.4 | 0011110010 | 1100001101 |
| Wakeup Special Code: | K29.7 | 1011101000 | 1011100111 |

The choice of the RD− K28.0 and K28.4 codes are used as the universal access code. After transmission, the RD remains negative. The command byte and length byte are next to be transmitted. The command and length bytes depend on the value of the DS command code (3) and the length. Using a length of 256 bytes (0x100) gives a command byte of 0x31 and a length byte of 0x00 (The least significant two bits of the command are the most significant bits of the length). The 0x31 command byte then becomes the 8b/10b code of D17.1 that is also bit balanced so the RD remains negative. The 0x00 length byte is the 8b10b code of D0.0 which converts to 1001110100, again this code is bit balanced so the RD remains negative. Now the wakeup special code K29.7 can be transmitted containing the RD− code of 101110 1000 repeatedly since the RD does not change. The CRC can take on its normal value and does not need to be considered here since it does not affect the RD of the data portion. Note that the alignment pattern is the 8b10b code K28.5 (001111 1010) since it is the comma character.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A telemetry system for enabling radio-frequency (RF) communications between an implantable medical device and an external device, comprising:
   an antenna, an RF transmitter, an RF receiver, and a controller incorporated into each of the implantable and external devices;
   a wakeup timer incorporated into the implantable device wherein the RF transmitter and receiver are interfaced to the controller in the implantable device to enable the RF transmitter and receiver to be powered up or down;
   wherein the external device is programmed to transmit a data segment containing a repeating sequence of special wakeup characters in order to establish a communications session with the implantable device;
   wherein the implantable device is programmed to power up its transmitter and receiver for a specified time window at periodic intervals defined by the wakeup timer and wait for receipt of one of the special wakeup characters transmitted by the external device;
   wherein the implantable device is programmed to maintain its transmitter and receiver in a powered-up state upon receipt of a special character and for as long as consecutive special wakeup characters continue to be received, to transmit an acknowledge signal to the external device upon receipt of at least one character other than a special wakeup character, and then to wait a specified period of time for a response from the external device;
   wherein the external device and the implantable device are programmed such that the external device transmits the data segment containing the repeating sequence of special wakeup characters in the context of a handshaking protocol for collision avoidance in which the external device transmits an RTS and a CTS frame before the data segment and in which the implantable device transmits an ACK frame in response; and,
   wherein the external device and the implantable device are programmed to establish a communications session when a response to the acknowledge signal is received by the implantable device.

2. The system of claim 1 wherein the RF transmitter and receiver of the implantable device are maintained in the powered-up state for the duration of the communications session.

3. The system of claim 1 wherein the implantable device and the external device communicate by a transmission code which provides a DC balanced data stream.

4. The system of claim 3 wherein the transmission code is 8b/10b.

5. The system of claim 3 wherein the wakeup special character is bit balanced and not changed by the transmission code.

6. The system of claim 1 further comprising a wakeup timer incorporated into the external device and wherein the external device is programmed to transmit a plurality of special wakeup characters to the implantable device in an attempt to establish a communications session at periodic intervals defined by its wakeup timer.

7. The system of claim 6 wherein the external device is programmed to adjust the periodic intervals at which it transmits a plurality of special wakeup characters to the implantable device after a successful communications session is established and data collected.

8. The system of claim 6 wherein the external device is programmed to establish a communications session and collect data from the implantable device on a daily basis.

9. The system of claim 8 wherein the external device is programmed to adjust the periodic intervals at which it transmits a plurality of special wakeup characters to the implantable device in accordance with the time of day at which past successful communications sessions were established.

10. The system of claim 6 wherein the external device is further programmed to transmit a plurality of special wakeup characters to the implantable device in an attempt to establish a communications session when a user command is received via a user interface.

11. A method by which an external device communicates with an implantable medical device via a wireless telemetry system, comprising:

transmitting a data segment containing a repeating sequence of special wakeup characters from the external device in order to establish a communications session with the implantable device, wherein the implantable device powers up its transmitter and receiver for a specified time window at periodic intervals and waits for receipt of one of the special wakeup characters transmitted by the external device;

wherein the implantable device maintains its transmitter and receiver in a powered-up state upon receipt of a special character and for as long as consecutive special wakeup characters continue to be received, transmits an acknowledge signal to the external device upon receipt of at least one character other than a special wakeup character, and then waits a specified period of time for a response from the external device;

wherein the external device transmits the data segment containing the repeating sequence of special wakeup characters in the context of a handshaking protocol for collision avoidance in which the external device transmits an RTS and a CTS frame before the data segment and in which the implantable device transmits an ACK frame in response; and, establishing a communications session when a response to the acknowledge signal is received by the implantable device.

12. The method of claim 11 wherein the implantable device and the external device communicate by a transmission code which provides a DC balanced data stream.

13. The method of claim 12 wherein the transmission code is 8b/10b.

14. The method of claim 13 wherein the wakeup special character is bit balanced and not changed by the transmission code.

15. The method of claim 11 further comprising transmitting a plurality of special wakeup characters to the implantable device in an attempt to establish a communications session at periodic intervals.

16. The method of claim 15 further comprising adjusting the periodic intervals at which the external device transmits a plurality of special wakeup characters to the implantable device after a successful communications session is established and data collected.

17. The method of claim 15 further comprising establishing a communications session and collecting data from the implantable device on a daily basis.

18. The method of claim 17 further comprising adjusting the periodic intervals at which the external device transmits a plurality of special wakeup characters to the implantable device in accordance with the time of day at which past successful communications sessions were established.

* * * * *